(12) United States Patent
Kaneko et al.

(10) Patent No.: US 9,340,533 B2
(45) Date of Patent: May 17, 2016

(54) 1,4-BENZOTHIAZEPINE-1-OXIDE DERIVATIVE AND PHARMACEUTICAL COMPOSITION UTILIZING THE SAME

(71) Applicant: Noburo Kaneko, Oyama-shi, Tochigi (JP)

(72) Inventors: Noburo Kaneko, Oyama (JP); Mitsuru Takahashi, Takatsuki (JP)

(73) Assignee: Kaneko Noboru, Oyama-shi (JP)

( * ) Notice: Subject to any disclaimer, the term of this patent is extended or adjusted under 35 U.S.C. 154(b) by 51 days.

(21) Appl. No.: 14/140,185

(22) Filed: Dec. 24, 2013

(65) Prior Publication Data

US 2014/0135313 A1    May 15, 2014

Related U.S. Application Data

(63) Continuation of application No. 13/203,188, filed as application No. PCT/JP2010/001219 on Feb. 24, 2010, now Pat. No. 8,642,586.

(30) Foreign Application Priority Data

Feb. 25, 2009    (JP) ................ 2009-066949
Sep. 28, 2009    (JP) ................ 2009-222610

(51) Int. Cl.
    *A61K 31/554*     (2006.01)
    *C07D 401/06*     (2006.01)
    *C07D 417/06*     (2006.01)

(52) U.S. Cl.
    CPC .................... *C07D 417/06* (2013.01)

(58) Field of Classification Search
    CPC ................ A61K 31/554; C07D 401/06
    USPC ................ 514/211.09; 540/552
    See application file for complete search history.

(56) References Cited

U.S. PATENT DOCUMENTS

2005/0215540 A1    9/2005    Marks et al.
2007/0049572 A1    3/2007    Marks et al.

FOREIGN PATENT DOCUMENTS

| JP | 4-230681 A | 8/1992 |
|---|---|---|
| JP | 2000-247889 A | 9/2000 |
| JP | 2001-031571 A | 2/2001 |
| JP | 2003-095977 A | 4/2003 |
| JP | 2009-506034 A | 2/2009 |
| WO | 92/12148 A1 | 7/1992 |
| WO | 2005/105793 A1 | 11/2005 |

OTHER PUBLICATIONS

International Search Report of PCT/JP2010/001219, mailing date Apr. 27, 2010.
Notification of Transmittal of Translation of the International Preliminary Report on Patentability (Form PCT/IB/338) of International Application No. PCT/JP2010/001219 mailed Oct. 27, 2011 with Form PCT/IPEA/409.

*Primary Examiner* — Brenda Coleman
(74) *Attorney, Agent, or Firm* — Westerman, Hattori, Daniels & Adrian, LLP (57) ABSTRACT

Provided are novel compound that is useful as a treatment agent or a prophylactic agent for cardiac failure, cardiac failure due to dystelectasis, left ventricular diastolic impairment, angina or cardiac infarct, hypertension, ischemic cardiac disease, and myocardial relaxation impairment recognized in cardiac failure, atrial fibrillation or ventricular arrhythmia, and a pharmaceutical composition containing the same. The invention pertains to a 1,4-benzothiazepine-1-oxide derivative represented by general formula [I] (In the formula, R represents a hydrogen atom or a hydroxyl group.) or a pharmaceutically acceptable salt thereof, and a pharmaceutical composition containing the same [I].

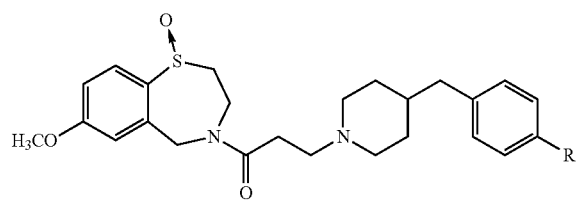

6 Claims, 2 Drawing Sheets

1,4-BENZOTHIAZEPINE-1-OXIDE DERIVATIVE AND PHARMACEUTICAL COMPOSITION UTILIZING THE SAME

CROSS-REFERENCE TO RELATED APPLICATIONS

The present application is a continuation of U.S. patent application Ser. No. 13/203,188, filed Aug. 24, 2011, which in turn is a U.S. National Stage Entry of International Application No. PCT/JP2010/001219, filed Feb. 24, 2010, which is based on and claims priority of Japanese Patent Application No. 2009-066949 filed Feb. 25, 2009, and Japanese Patent Application No. 2009-222610, filed Sep. 28, 2009, the entirety of each of which is incorporated herein by reference.

TECHNICAL FIELD

The present invention provides a 1,4-benzothiazepine-1-oxide derivative represented by the general formula [I] or a pharmaceutically acceptable salt thereof, and a pharmaceutical composition comprising thereof.

BACKGROUND ART

The heart has a pumping mechanism consisting of periodic contraction and relaxation functions in the myocardium, which provides blood to the internal organs and tissues of the whole body through a process where the blood is constantly circulating and returning to the heart. This process is a constant, periodic action in which the myocardium is supplied the necessary oxygen and nutrition from coronary circulation of the right and left coronary arteries. In a normal functioning myocardium, the oxygen supply and consumption are maintained in the homeostatic state.

When the myocardium is unable to contract and relax properly resulting in damage to the pumping function, congestion in the general organs and tissues is induced and heart failure occurs. During heart failure, activation of the sympathetic nervous system occurs, as well as increased levels of norepinephrine in the blood, leading to an increase in heart rate.

Presently, there are drug treatments for heart failure such as β-blockers that decrease heart rate, and lessen the contractility force, resulting in a decrease of oxygen consumption required from the myocardium. However, at high doses, β-blockers increase the risk for heart failure and must be used or administered with caution.

The myocardium contracts and relaxes regularly and periodically. This cardiac cycle is divided into two phases; systolic phase and diastolic phase. The systolic phase is from the mitral valve closure to the aortic valve closure and the diastolic phase is from the aortic valve closure to the mitral valve closure. Moreover, diastolic phase has 4 stages; isovolumic relaxation, rapid left ventricular filling, slow left ventricular filling, and atrial contraction. In the latter 3 stages among the 4 stages; rapid left ventricular filling, slow left ventricular filling, and atrial contraction, the ventricular myocardium expands more and blood inflow from atrium to ventricle occurs. The diastolic function of the ventricle has important significance on the cardiac function. When myocardial expansion is impaired, the blood inflow to the ventricle is hindered and then heart failure, especially heart failure due to diastolic dysfunction, occurs. Moreover, blood flows from the coronary artery into the myocardial tissues during diastolic phase, which is different from that of other organs. The diastolic blood flow is remarkably more from the left coronary artery than the right coronary artery. Therefore, the diastolic impairment of left ventricle induces disturbance of coronary flow into the left ventricular myocardial tissues, generates myocardial ischemia, and as a result aggravates heart failure due to diastolic dysfunction.

Moreover, left ventricular diastolic impairment occurs in elderly people and in patients with hypertension and cardiac hypertrophy even without the presence of heart failure. Left ventricular diastolic impairments can easily be diagnosed using Doppler echocardiography. Some patients with left ventricular diastolic impairment complain of symptoms including fatigue, shortness of breath, chest discomfort and chest pain. During prolongation of left ventricular diastolic impairment, impairment of the cardiomyocytes and fibrosis in the myocardium eventually induce heart failure.

To maintain normal functions of the heart, the appropriate amounts of oxygen and nutrients required are supplied to the myocardium through coronary perfusion by the left and right coronary arteries. The contraction and relaxation of the myocardium requires the oxygen and nutrients to function properly.

The drugs used to dilate the coronary arteries leads to an increase of oxygen supply to the myocardium, thus reducing the risk of myocardial ischemia. Myocardial oxygen consumption is determined by the heart rate and cardiac contractility, and that drug decreases oxygen consumption by reducing heart rate and myocardial contractility, lowering the risk of myocardial ischemia. A drug capable of dilating the coronary artery combined with decreasing heart rate and contractility, is a treatment agent or a prophylactic agent for ischemic heart disease, such as angina pectoris and myocardial infarction.

Heart failure is divided into systolic failure and diastolic failure. In systolic failure, the left ventricular minimum diastolic pressure and left ventricular diastolic pressure both increase, therefore the drug reinforcing the left ventricular diastolic function is comprised of an agent that leads to the improvement of systolic failure.

Furthermore, a drug is a treatment agent for angina pectoris and myocardial infarction because it dilates the coronary artery and then enhances the oxygen supply to the myocardium. The consumption of oxygen from the myocardium is dependent upon the contractility force and heart rate. It is comprised of a drug that is a prophylactic agent for ischemic heart disease, such as angina pectoris and myocardial infarction. The β-blocker is a treatment agent for angina pectoris and myocardial infarction, however, it does not have the effect to dilate the coronary arteries or increase left ventricular diastolic function.

A drug, reinforcing the left ventricular diastolic function, decreasing heart rate, increasing reduction of contractility, combined with dilation of the coronary artery, is comprised of a treatment agent or a prophylactic agent for heart failure due to diastolic dysfunction.

Moreover, the relaxant function in the heart is equally important as systolic function and diastolic function. Relaxation is the main component in the first stage among the four stages of the diastolic phase; the function of isovolumic relaxation, which is able to be estimated using the maximal negative first derivative of the left ventricular pressure ($-dP/dt$) and the disturbance of relaxant function is able to be detected in the left ventricular wall motion by using Doppler echocardiography.

Heart failure is induced by numerous complexities such as myocardial systolic impairment, relaxation impairment, or diastolic impairment. Diastolic heart failure is generally formed with the complexities of diastolic impairment and relaxant impairment. Relaxant impairment is recognized in ischemic heart disease, atrial fibrillation, and ventricular arrhythmia and worsens severely, resulting in decreased cardiac contractility. The improvement of myocardial relaxant function is essential for the treatment of ischemic heart disease, atrial fibrillation, and ventricular arrhythmia. Relaxation impairment worsens severely and "Rigor" occurs, not allowing relaxation. Deterioration of relaxation impairment leads to heart failure.

Myocardial relaxation impairment is recognized in ischemic heart disease, hypertensive heart disease, heart failure, atrial fibrillation, and ventricular arrhythmia. There are still no drugs that allow a relaxant effect on the myocardium. Catecholamines such as epinephrine and norepinephrine (NE) stimulate to take the calcium uptake of the sarcoplasmic reticulum and promote myocardial relaxation. However, those substrates also increase heart rate and blood pressure, resulting in enhancement of myocardial oxygen consumption. It is difficult to use the treatment agents for the disease mentioned. The ideal drug is a myocardial relaxant which promotes myocardial relaxation without changing the heart rate. It is an agent that does not change heart rate and accelerates myocardial relaxation, and an agent which can improve ischemic heart disease, hypertensive heart disease, heart failure, atrial fibrillation, and ventricular arrhythmia, and cardiac function.

Blood pressure is determined by cardiac output, peripheral blood resistance, circulation blood volume, and blood viscosity. Norepinephrine increases the peripheral vascular resistance and raises blood pressure. It is a treatment agent or a prophylactic agent used to decrease blood pressure for hypertension due to norepinephrine-loaded hypertension.

Meanwhile, 4-[3-(4-benzylpiperidin-1-yl)propionyl]-7-methoxy-2,3,4,5-tetrahydro-1,4-b enzothiazepine and derivatives thereof have been reported to have the effective compounds which inhibit myocardial necrosis including kinetic cell death (KD) and acute myocardial infarction without cardiac suppressive effects (Patent Documents 1 and 2). There have been many reports regarding its effectiveness on atrial fibrillation as well as its anticancer properties, for example, use for the treatment of atrial fibrillation (Patent Document 3), enhancement of anti-cancer agents for the treatment of cancer (Patent Document 4), use for the improvement or stabilization of the ryanodine receptor function, $Ca^{2+}$ leak from the sarcoplasmic reticulum (Patent Document 5), muscle relaxation accelerator, treatment for left ventricular relaxation disturbance, treatment for angina pectoris, treatment for acute pulmonary emphysema, for improvement of microcirculation blood flow, for hypertension, for ventricular tachycardia and torsades de pointes (Patent Document 6).

PRIOR ART DOCUMENTS

Patent Documents

Patent Document 1: Japanese Patent Application Laid-Open (JP-A) No. 4-230681
Patent Document 2: WO 92/12148
Patent Document 3: JP-A No. 2000-247889
Patent Document 4: JP-A No. 2001-31571
Patent Document 5: JP-A 2003-95977
Patent Document 6: WO 2005/105793

SUMMARY OF THE INVENTION

Problems to be Solved by the Invention

The present invention provides a novel pharmaceutical composition for treatment agent enhancing cardiac relaxation and improving myocardial relaxation impairment, and a therapeutic agent of relaxation of the vascular smooth muscle and hypertension by decreasing blood pressure. Moreover, it accelerates relaxation of skeletal muscle and uterine smooth muscle and provides a compound as a treatment agent or a prophylactic agent for muscle hypertonia and miscarriage.

Furthermore, the present invention provides a novel compound that is useful as a treatment agent or a pharmaceutical compound containing the same for improving cardiac relaxation without changing heart rate.

Means for Solving the Problems

The present inventor has been researching several pharmacological effects of 4-[3-(4-benzylpiperidin-1-yl)propionyl]-7-methoxy-2,3,4,5-tetrahydro-1,4-benzothiazepine and derivatives thereof. These compounds have been reported to have extremely significant pharmacological effects in the citations listed above. The present inventor urged more research and found that its sulfur (S)-oxide derivatives have similar effects as the basic free compound and specific pharmacological effects not found in the basic free compound.

That is, the present invention provides a novel 1,4-benzothiazepine-1-oxide derivative represented by the following general formula [1]:

[I]

(wherein, R is a hydrogen atom or a hydroxyl group.)
and a pharmaceutically acceptable salt thereof.

The present invention also provides a pharmaceutical composition comprising the 1,4-benzothiazepine-1-oxide derivative or a pharmacologically acceptable salt thereof, and a pharmacologically acceptable carrier.

The present invention includes contents explained in detail below.

(1) A 1,4-benzothiazepine-1-oxide derivative represented by the following general formula [I]:

[I]

(wherein, R is a hydrogen atom or a hydroxyl group.)
and a pharmaceutically acceptable salt thereof.

(2) The 1,4-benzothiazepine-1-oxide derivative according to (1), wherein the pharmaceutically acceptable salt of 1,4-benzothiazepine-1-oxide-derivative in an oxalate.

(3) A pharmaceutical composition comprising the 1,4-benzothiazepine-1-oxide derivative according to (1) or (2), or the pharmaceutically acceptable salt thereof and the pharmacologically acceptable carrier.

(4) The pharmaceutical composition according to (3), wherein the pharmaceutical composition is a treatment agent or a prophylactic agent for cardiac disease and hypertension.

(5) The pharmaceutical composition according to (4), wherein the cardiac disease includes cardiac failure, angina pectoris or myocardial infarction.

(6) The pharmaceutical composition according to (5), wherein cardiac failure includes left ventricular diastolic impairment or cardiac relaxation impairment.

(7) The pharmaceutical composition according to (4), wherein the hypertension is due to the effect of decreasing blood pressure during high blood pressure.

(8) The pharmaceutical composition according to (3), wherein the pharmaceutical composition is a treatment agent or a prophylactic agent for myocardial relaxation impairments due to complications of ischemic heart disease, hypertension cardiac disease, heart failure, atrial fibrillation, and ventricular arrhythmia, by promoting acceleration of myocardial relaxation without changing heart rate.

(9) A pharmaceutical composition according to any one of (3) to (8), wherein the 1,4-benzothiazepine-1-oxide derivative or a pharmaceutically acceptable salt thereof is generated in vivo by administering a 1,4-benzothiazepine derivative or a pharmaceutically acceptable salt thereof represented by the following formula [II]:

[II]

-CH2CH2-N-piperidine-CH2-phenyl-R)

(wherein, R is a hydrogen atom or a hydroxyl group.)
to a subject as a maternal compound of the 1,4-benzothiazepine derivative represented by the following formula [I].

(10) A method of producing a 1,4-benzothiazepine-1-oxide derivative represented by the following general formula [I]:

[I]

![Structure I](H3CO-benzothiazepine-1-oxide-N-C(O)-CH2CH2-N-piperidine-CH2-phenyl-R)

(wherein, R is a hydrogen atom or a hydroxyl group.)
and a pharmaceutically acceptable salt thereof comprising a step by oxidizing a 1,4-benzothiazepine derivative represented by the following formula[II]:

(wherein, R is a hydrogen atom or a hydroxyl group.).

(11) A method of producing a 1,4-benzothiazepine derivative according to (10), wherein the oxidation carries out in the presence of peracid as a oxidation agent.

(12) A use of a 1,4-benzothiazepine-1-oxide derivative or a pharmaceutically acceptable salt thereof represented by the general formula [I] described above to produce a treatment agent or a prophylactic agent for cardiac disease or hypertension.

(13) A use of a 1,4-benzothiazepine-1-oxide derivative or a pharmaceutically acceptable salt thereof represented by the general formula [I] described above to produce a treatment agent or a prophylactic agent for cardiac failure due to myocardial relaxation impairment.

(14) A use according to (12) or (13), wherein a 1,4-benzothiazepine-1-oxide derivative or a pharmaceutically acceptable salt thereof represented by the general formula [I] described above, is generated in vivo by administering a 1,4-benzothiazepine derivative or a pharmaceutically acceptable salt thereof represented by the general formula [II] described above.

(15) A 1,4-benzothiazepine-1-oxide derivative or a pharmaceutically acceptable salt thereof represented by the general formula [I] described above to be used for a treatment agent or a prophylactic agent for cardiac disease or hypertension.

(16) A 1,4-benzothiazepine-1-oxide derivative or a pharmaceutically acceptable salt thereof represented by the general formula [I] described above to be used for a treatment agent or a prophylactic agent for cardiac failure due to myocardial relaxation impairment.

(17) A method of treatment of cardiac disease and hypertension by administrating an effective dose of a pharmaceutical composition comprising of a 1,4-benzothiazepine-1-oxide derivative or a pharmaceutically acceptable salt thereof represented by the general formula [I] described above to a patient with cardiac disease or hypertension.

(18) A method of treatment of cardiac failure due to myocardial relaxation impairment by administrating an effective dose of a pharmaceutical composition comprising of a 1,4-benzothiazepine-1-oxide derivative or a pharmaceutically acceptable salt thereof represented by the general formula [I] to a patient with cardiac failure due to myocardial relaxation impairment.

While the compound of the present invention represented by general formula [I] or a salt thereof is thought to be metabolized in vivo from the general formula [II] of the basic compound or a salt thereof, the present inventor has produced the compound of the general formula [I], discussed in detail the properties, and firstly found that the concerned compound represented by the general formula [I] possesses useful pharmacological effects.

Moreover, the compound of the present invention represented by the general formula [I] or a salt thereof is different from the basic compound represented by the general formula [II] or a salt thereof, regulates the cardiac relaxant function without increasing the heart rate, and is considered to have different pharmacological effects compared to the basic compound represented by the general formula [II] or a salt thereof.

It is difficult even for the cardiologist to know how to treat diseases using β-blockers because it reduces myocardial contractility and decreases heart rate. It is generally recommended to use treatment at low doses since administration at a high dose is dangerous. The $Ca^{2+}$ antagonist dilates the coronary artery and rapidly decreases blood pressure and it is also generally recommended for treatment at low doses since administration at a high dose is dangerous. For safety concerns and requirements, mild agents are best used for dilatation of the coronary artery, suppressive effects on cardiac contraction, and decrease in heart rate.

The present inventor has been found that the compound of the present invention represented by the general formula [I] or the salt thereof possesses the ability to increase left ventricular diastolic function, dilate the coronary artery, reduce myocardial contractility, mildly decrease heart rate, and is useful for cardiac failure, cardiac failure due to diastolic dysfunction, left ventricular diastolic impairment, angina pectoris, or myocardial infarction. Moreover, the compound of the present invention has been found to be useful as a treatment agent to improve the cardiac relaxant function without changing heart rate for ischemic heart disease, hypertensive heart disease, cardiac failure, atrial fibrillation, and ventricular arrhythmia.

And, it has been found that the compound of the present invention represented by the general formula [I] or a salt thereof has the mild effect to improve myocardial diastolic function, dilate the coronary arteries, decrease heart rate and decrease cardiac contractility.

The present inventor discovered that the compound of the present invention possesses useful effects for improvement of left ventricular diastolic function and inhibits norepinephrine-induced left ventricular diastolic impairment.

The present invention provides the compound of the present invention as a useful agent to improve left ventricular diastolic function, cardiac failure and diastolic failure, wherein physical signs of an increase in left ventricular minimum diastolic pressure and left ventricular end-pressure are present.

The present invention provides a useful agent of treatment and prevention wherein the compound of the present invention is administered to the elder person and patients with hypertension and cardiac hypertrophy, and for the improvement of left ventricular diastolic impairment in patients with physical signs of left ventricular diastolic impairment. In the present invention, the compound of the present invention is provided as a safe, useful agent to patients of angina pectoris with significant constriction of coronary artery and myocardial infarction. Moreover, the present invention is provided by the compound of the present invention as a useful treatment agent or a prophylactic agent to improve myocardial relaxation impairment combined with ischemic heart disease, hypertensive heart disease, cardiac failure, atrial fibrillation, and ventricular arrhythmia.

Therefore, the present invention provides a novel compound which is useful, and a pharmaceutical compound containing these compounds of the present invention.

Moreover, the compound of the present invention represented by the general formula [I] or a salt thereof is considered the basic compound represented by the general formula [II] or the metabolite of the salt in vivo. So, the pharmaceutical compound of the present invention is able to use the basic compound represented by the general formula [II] or a salt thereof as the pro-drug instead the present invention represented general formula [I] and the basic compound represented by the general formula [II].

Effects of the Invention

The compound of the present invention itself possesses the effects to improve myocardial diastolic function, to mildly dilate the coronary artery, decrease heart rate, and increase the oxygen supply by decreasing myocardial oxygen consumption. Therefore, the present invention provides a novel pharmaceutical compound that is useful as a treatment agent and a prophylactic agent in a safe and desirable manner for the elder person and patients with hypertension and cardiac hypertrophy, patients of cardiac failure due to diastolic failure, angina pectoris and myocardial infarction, and for those who have bad prognoses and are conventionally difficult to treat.

In addition, the compound of the present invention possesses the ability to improve cardiac relaxation without changing heart rate and is useful for myocardial relaxant impairment. The compound of the present invention is useful as a treatment agent or a prophylactic agent for hypertension. Moreover, the compound of the present invention is useful as a treatment agent or a prophylactic agent for improving myocardial relaxation impairment combined with ischemic heart disease, hypertensive heart disease, cardiac failure, atrial fibrillation, and ventricular arrhythmia.

The present pharmaceutical compound may be administered through oral, sublingual, transdermal patch, and intravenous methods, or infused into the coronary artery to eliminate spasms after inducing it diagnostically, and as well as treatment and prevention of coronary spasms.

Moreover, the compound of the present invention is able to allow lower dosages of β-blockers and $Ca^{2+}$ antagonists for treatment or prevention of angina pectoris, especially myocardial ischemia on angina pectoris, and for treatment or prevention against cardiac failure, especially cardiac failure due to diastolic failure.

MODES FOR CARRYING OUT THE INVENTION

The present invention provides a 1,4-benzothiazepine-1-oxide derivative represented by the following general formula [I] or a pharmaceutically acceptable salt thereof:

[I]

(wherein, R is a hydrogen atom or a hydroxyl group.)

The preferred examples of the present invention include a 4-[3-4-benzylpiperidin-1-yl)propionyl]-7-methoxy-2,3,4,5-tetrahydro-1,4-benzothiazepine-1-oxide or a pharmaceutically acceptable salt thereof represented by the following formula [III]:

(III)

and a 4-{3-[4-(4-hydroxybenzyl)piperadin-1-yl]propionyl}-7-methoxy-2,3,4,5-tetrahydro-1,4-benzothiazepine-1-oxide represented by the following formula [IV] or a pharmaceutically acceptable salt thereof.

[IV]

The compound of the present invention contains the basic nitrogen atom at positions where it is able to form the addition of acid salts. Formations of the addition of acid salts are not particularly limited, as long as they are of pharmaceutically acceptable material. The compound of the present invention favors the addition of specific acid salts such as inorganic acid salts; hydrochloride, hydrobromate, sulfate, phosphate, nitrate, and the addition of organic acid salts; oxalate, acetate, propionate, succinate, glycolate, lactate, malate, tartrate, citrate, maleic acid salts, fumarate, methanesulfonate, benzenesulfonanate, p-toluenesulfonate, and ascorbate. Hydrate is also a good solvent for the compound of the present invention or the acid salt addition.

In the compound of the present invention, the heterocyclic sulfur (S) and oxygen (O) bond, that is, forms the polar atomic group indicated by strong electric negativity and is also the coordinate bond. Regarding the sulfur and oxygen bond, the coordinate bond can be represented with an arrow; "heterocyclic sulfur (S)→oxygen (O) and this coordinated bond can be represented as "heterocyclic $S^+$—$O^-$".

The compound of the present invention represented by the general formula [I] is able to be produced by the oxidation by the proper oxidation agents of the compound represented by the general formula [II]. Peracids, for example, peracetic acid, perbenzoic acid, and meta-chloroperoxybenzoic acid (mCPBA) can be used as the oxidation agents. Preferred solvents are halogenated hydrocarbon such as methylene chloride and chloroform may be used. The reaction temperature is preferably maintained low, between 0-5° C., to prevent oxidation to the final sulfonation. The objective material can be isolated and purified from the reaction mixture by the known steps of isolation and purification using the extractive procedure, chromatography and distillation.

For example, the compound, 4-[3-4-benzylpiperidin-1-yl)propionyl]-7-methoxy-2,3,4,5-tetrahydro-1,4-benzothiazepine-1-oxide represented by the formula [III] of the present invention is able to be produced as shown in the following procedure:

by an oxidation of the heterocyclic sulfur in the 4-[3-(4-benzylpiperidin-1-yl)propionyl]-7-methoxy-2,3,4,5-tetrahydro-1,4-benzothiazepine of the compound [V] by the oxidant, for example, meta-chloroperoxybenzoic acid (mCPBA) in a chloroform ($CHCl_3$) solvent.

The compound of the present invention, 3-4-benzylpiperidin-1-yl)propionyl-7-methoxy-2,3,4,5-tetrahydro-1,4-benzothiazepine-1-oxide, which is produced by an oxidation of the hydrochloride salt represented by formula [V] by the oxidant, isolated by silica gel chromatography using chloroform-methanol as a solvent, followed by removed the solvent from the chloroform-methanol solution by azeotropic distillation, and finally removed by the residual solvent in argon. The purity of compound presented by formula [III], thus obtained is 90% or higher, and a molecular weight (mw) of the compound is 440.61. The compound is amorphous, stable against exposure of oxygen, humidity, acid and alkali at room temperature, is easily dissolved in ethanol and dimethysulfoxide (DMSO), and irritating to the skin. The oxalate salt of the compound [III] of the present invention has a mw of 530.65, the purity is 90% or higher. The salt is solid with melting point at 167-168° C., and is able to be dissolved in water, ethanol, DMSO. The compound has stereoisomers in the amide form, is confirmed to exist at the rate of about 2:3 in of amide parts using H-NMR analysis at room temperature.

The compound 4-{3-[4-(4-hydroxybenzyl)piperadin-1-yl]propionyl}-7-methoxy-2,3,4,5-tetrahydro-1,4-benzothiazepine-1-oxide represented by the formula [IV] or a pharmaceutically acceptable salt thereof is produced by preserving a hydroxyl group in necessary situations, by a similar oxidative reaction. The basic 1,4-benzothiazepine derivative was administered to either a rat or dog, then the urine and excrement was obtained, adding water for homogenization. The compound was isolated from the obtained supernatant by high performance liquid chromatography (HPLC) using a reverse column with silica gel (ODS) chemically bounded with octadecyl group; and gradient isolations as a mobile phase: solution A is water with 0.1% trifluoroacetic acid (TFA) and solution B is acetonitrile with 0.1% trifluoroacetic acid (TFA). The retention time was about 19-22 minutes. MS (m/z): 457. The compound [III] was isolated using HPLC with gradient isolation using the procedure similar to the compound [IV] of the present invention and obtained within 27-30 minutes of the retention time.

The compound of the present invention represented by the formula [I] or a salt thereof is useful as a treatment agent or a prophylactic agent for heart disease, including heart failure, angina pectoris, myocardial infarction, or hypertension, and moreover, is useful as a treatment agent or a prophylactic agent for heart failure due to diastolic dysfunction, left ventricular relaxation impairment, improving the cardiac diastolic function and improving ischemic heart disease, hypertensive heart disease, cardiac failure, atrial fibrillation, and ventricular arrhythmia without changing the heart rate.

Therefore, the compound of the present invention represented by the formula [I] or a salt thereof is used as an active ingredient of pharmaceutical composition. The pharmaceutical composition of the present invention is administered orally and sublingually, transdermally, intravenously, and injected into the coronary artery to prevent coronary artery spasms after inducing it diagnostically, as well as treatment and prevention of coronary spasms. Moreover, the treatment and prevention of the compound of the present invention allows a decrease in the dosage of treatments using β-blockers and $Ca^{2+}$ antagonists.

The active ingredient of the present pharmaceutical composition is obtained from the maternal compound represented by the general formula [II] or a salt thereof in vivo as the pro-drug as described in the experimental data. Therefore, the active ingredient in the pharmaceutical composition of the present invention may be the compound represented by the general formula [II] or a salt thereof as the pro-drug instead of the compound represented by the formula [I] or a salt thereof. The compound of the present invention represented by the general formula [I] is obtained in vivo as the metabolite of the basic compound of the present invention represented by the general formula [II] or a salt thereof, and is able to be used as the pro-drug as described in the experimental data.

Solid dosage forms for oral administration of the present invention include tablet, pill, powder and granule forms. The solid compound can be produced under a standard procedure using the active material combined with an inactive dilute agent, dispersion agent, or absorbent such as lactate, mannitol, glucose, hydropropyl cellulose, slightly-crystalline cellulose, starch, polyvinylpyrolidone, magnesium metasilicic aluminate, or silicic anhydride powder.

For preparation of solid dosage forms such as a tablet or pill, it is recommended to use a coating membrane consisting of a gastric acid-soluble or an intestine-soluble material substance such as sucrose, gelatin, hydroxypropyl-cellulose, hydroxymethyl cellulose phthalate, or a two-layer coating membrane. Moreover, it is able to be made from a capsule such as gelatin or ethylcellulose.

Liquid dosage forms for oral administration of the present invention include pharmaceutically acceptable emulsions, solutions, suspensions, syrups, or elixir agents. Dilating agents, such as distilled water, ethanol, vegetable oil or other emulsions are best recommended to be mixed with subsidiary agents aside from dilating agents such as wetting agents, suspending agents, sweetening agents, flavoring agents, aromatic agents, or preservatives for this compound.

Non-oral injection preparations of the compound include abacterial or sterile water, non-aqueous solution, emulsifying agents and suspending agents. Aqueous solutions, solutions, and emulsions used for the injection include distilled water, physiological salt solutions, cyclodextrin and derivatives thereof, organic amines such as triethanolamine, diethanolamine, monoethanolamine, and triethylethylamine, or inorganic alkali solutions.

In the case of producing a water-soluble agent, it is better to use vegetable oils such as propylene-glycol, polyethylene-glycol or olive oil, and an alcohol such as ethanol. Soluble agents include surface-active agents such as polyoxyethyl consolidated castor oil, sucrose-fatty acid-esters (formation of mixed micelle) or lecithin, and lecithin in aqueous solution (liposomal formation). The emulsification agent is able to be made from the water-insoluble solutions such as vegetable oils, lecithins, polyoxyethyl consolidated castor oil, polyoxyethylene, or polyoxypropylene-glycol.

The compound of the present invention represented by the general formula [I] or a salt thereof, or the compound of the pro-drug represented by the general formula [II] or a salt thereof is able to be administered between 0.1 mg to 1 g, at the proper range of 1 mg-1 g or 0.1 mg-0.5 g, once to several times a day through oral or non-oral methods. However, the methods of administration, treatment time and effects of treatment may vary based on differences in age, body weight, and symptoms.

The present invention is described in practice 1 below, which is set forth to aid in the explanation and understanding of the invention, with non-limiting preferred embodiments of the invention.

EXAMPLE 1

Production of 4-[3-(4-benzylpiperidin-1-yl)propionyl]-7-methoxy-2,3,4,5-tetrahydro-1,4-benzothiazepine-1-oxide represented by the formula [III] of the present invention 30.0 g of 4-[3-(4-benzylpiperidin-1-yl)propionyl]-7-methoxy-2,3,4,5-tetrahydro-1,4-benzothiazepine hydrochloride represented by the formula [V] and 800 ml of chloroform ($CHCl_3$) as a solvent were added to a reactor and stirred at room temperature until dissolved. Then, the reaction mixture was cooled to 0-1° C. by ice-cold water bath. Then 14.0 g of meta-chloroperoxybenzoic acid (mCPBA) in 600 ml of $CHCl_3$ solution was gradually added by dropwise to the solution within 110 minutes while maintaining the reaction temperature. After the dropping, the mixture was stirred for about 20 minutes at 0-1° C.

Then, 4.14 g of $Na_2SO_3$ in 200 ml of $H_2O$ solution was added to the reaction mixture by dropwise in 1 minute at 0-5° C., and stirred for 10 minutes at 0-5° C. Subsequently, sodium hydroxide (NaOH) solution (1 mol/L) was dropwised for 1 minute while maintaining a cool temperature. After the dropwise, the reaction mixture was stirred for 15-20 minutes at 0-5° C. After the reaction, organic layer was separated, washed the remaining aqueous layer by 600 ml chloroform ($CHCl_3$). The two organic layers were combined and washed with 200 ml of $H_2O$ once and then washed with 200 ml of saturated NaCl solution once. The organic layer was dried with anhydrate $Na_2SO_4$ and concentrated under reduced pressure.

The residue was purified by silica gel chromatography using ethanol. 13 g of the objective material was obtained as a viscous amorphous or oil.

IR ($cm^{-1}$): 3452, 2919, 1643, 1594, 1022
$^1$H-NMR ($CDCl_3$ 300 MHZ): δ
1.1-2.95 (17H, m), 3.78 (3H, s), 3.86-4.16 (2H, m), 4.65 (2H, s), 6.8-7.65 (8H, m)
MS (FD-MS): 441 ($M^+$)

EXAMPLE 2

Production of the Compound [IV] of the Present Invention

Using three male Sprague Dawley rats, 0.3 mg/kg of a maternal compound of the chemical compound [IV] was intravenously administered. Their urine and excrement were obtained 24 hours after administration. Water was added to the excrement for homogenization. Then the pooled samples for the three cases were treated for measurement.

2 g of the pooled excrement sample was mixed with 4 ml of acetonitrile, stirred, centrifuged and the supernatant was extracted. The obtained supernatant was concentrated and dried at 40° C. under a stream of nitrogen gas. The dried material was dissolved in acetonitrile and water. The resulting solution was analyzed using liquid chromatography mass spectrometry (LC/MS) and the excluding material was obtained within 21-22 minutes of the retention time. LC/MS (m/z): 457.

The urine sample was centrifuged and then the supernatant was analyzed using LC/MS. The excluding material was obtained within 21-22 minutes of the retention time. LC/MS (m/z): 457.

EXAMPLE 3

Experiment 1

Effect of the Compound [III] of the Present Invention for LV Diastolic Function in Normal Rat (1) After breeding for 1 week, male Wistar rats were anesthetized with 3% isoflurane inhalation, followed by an insertion of a tube in the trachea and respiration subsequently controlled with an artificial ventilator using 1.7% isoflurane for maintained anesthetization. A micrometer-tipped pressure catheter (Manufactured by 2F, Millar Instruments) was inserted from the right common carotid artery into the left ventricle (LV) and a polyethylene catheter (SP10) was inserted into the right femoral vein for the compound of the present invention or physiological salt solution (PSS) injections. After confirming stable hemodynamics for 10 minutes, LV minimum diastolic pressure and LV end-diastolic pressure was counted every minute. The compound [III] (0.1 mg/kg/min) of the present invention or PSS was infused at 16.6 μL/min for 10 minutes in the test and control groups, respectively.

LV minimum diastolic pressure and LV end-diastolic pressure was counted every minute for 20 heart beats before and after administration of the compound. LV minimum diastolic pressure and LV end-diastolic pressure before administration was set at 100% and the data of each after administration was calculated as a percentage change from before administration. Data is shown as mean and standard deviation. The results are shown in Table 1 and 2.

TABLE 1

Measurement of LV minimum diastolic pressure and end-diastolic pressure before and after administration of physiological salt solution (PSS)

|  | Before administration of PSS | After administration of PSS |
|---|---|---|
| LV minimum diastolic pressure | 100% | 101.6 ± 4.5% |
| LV end-diastolic pressure | 100% | 102.0 ± 5.2% |

LV minimum diastolic pressure and LV diastolic end-diastolic pressure did not decrease after the administration of PSS.

LV minimum diastolic pressure and LV diastolic end-diastolic pressure before and after the compound [III] of the present invention is indicated in Table 2.

TABLE 2

Measurement of LV minimum diastolic pressure and end-diastolic pressure before and after administration of the compound [III] of the present invention

|  | Before administration of compound [III] | After administration of compound [III] |
|---|---|---|
| LV minimum diastolic pressure | 100% | 76.0 ± 5.2% |
| LV end-diastolic pressure | 100% | 78.4 ± 6.6% |

LV minimum diastolic pressure and LV diastolic end-diastolic pressure in normal rats clearly decreased after administration of compound [III]. From the result, the compound of the present invention possesses the ability to improve LV diastolic dysfunction.

EXAMPLE 4

Experiment 2

Effect of LV Diastolic Dysfunction of the Compound [III] of the Present Invention for the Chronic Infarct Rat Male Wistar rats were used. After induction of anesthesia with 3% isoflurane inhalation, a polyethylene tube was inserted into the trachea. Respiration was subsequently controlled with an artificial ventilator with maintenance of anesthesia using 1.7% isoflurane. The chest was opened at the left third intercostals space and the pericardial membrane was incised. The left anterior descending coronary artery (LAD) was completely ligated with silk string (6.0, Ethicon) in the infarction group. Following this procedure, the chest was immediately closed, the inserted tube in the trachea was removed, and subjects returned to the breeding room after arousal.

Two months after operation, animals were again anesthetized and intubated as described above. A micronanometer-tipped pressure catheter (2F, Millar Instruments) was inserted into the right common carotid artery into the left ventricle (LV) and a polyethylene catheter (SP10) for solution injection was inserted from the right femoral vein to infuse the physiological salt solution (PSS) or test compound solutions. After confirming stable hemodynamics for 10 minutes, 20 μg/kg/min of norepinephrine was infused for 30 minutes in the chronic infarction group. The results of the production of norepinephrine-induced dysfunction in chronic infarction are indicated in Table 3. The invention compound [III] (0.1 mg/kg/min) and PSS were infused for 10 minutes after 20 minutes of administration of norepinephrine at 16.6 μL/min for test and control groups, respectively. LV minimum diastolic pressure and LV end-diastolic pressure was counted every minute for 20 heart beats. The area of myocardial infarction (infarction size) in rats was estimated using the modified method of Sandmann et al (*J Cardiovasc Pharmacol* 2000; 37; 64-77.) for administration of the compound of the present invention and PSS. That is, the infarct size (%) was estimated using the followed formula:

$$\text{myocardial infarction area (\%)} = \left[ \frac{\left(\frac{\text{epicardial infarct length} + \text{endocardial infarct length}}{2}\right)}{\left(\frac{\text{total } LV \text{ epicardial circumference} + \text{total } LV \text{ endocardial circumference}}{2}\right)} \right] \times 100$$

The infarct size in the invention compound group and PSS group were almost of similar sizes at 24% and 26%, respectively.

LV minimum diastolic pressure and LV end-diastolic pressure before administration was set at 100% and the data of each after administration was calculated as a percentage change from before administration. Data is shown as means and standard error. The following results are shown in Table 4 (control) and Table 5 (the compound), respectively.

TABLE 3

Production of norepinephrine-induced diastolic dysfunction in chronic infarction

| (mmHg) | Before administration of Norepinephrine | After administration of Norepinephrine |
|---|---|---|
| LV minimum diastolic pressure | 4.5 ± 0.8 | 18.5 ± 1.2 |
| LV end-diastolic pressure | 6.5 ± 0.7 | 25.8 ± 1.1 |

After the administration of norepinephrine, LV minimum diastolic pressure and LV end-diastolic pressure clearly increased in chronic infarction rats, which indicated occurrence of the diastolic impairment.

TABLE 4

Measurement before and after administration of physiological salt solution (PSS)

|  | Before administration of PSS | After administration of PSS |
|---|---|---|
| LV minimum diastolic pressure | 100% | 104.6 ± 4.8% |
| LV end-diastolic pressure | 100% | 105.0 ± 5.1% |

For norepinephrine-induced LV diastolic dysfunction in chronic infarct rats, LV minimum diastolic pressure and LV end-diastolic pressure did not decrease after infusion of PSS.

TABLE 5

Measurement before and after administration chemical compound [III] of the present invention

|  | Before administration of compound [III] | After administration of compound [III] |
|---|---|---|
| LV minimum diastolic pressure | 100% | 76.0 ± 5.2% |
| LV end-diastolic pressure | 100% | 78.4 ± 6.6% |

LV diastolic impairment was induced by a norepinephrine infusion to chronic infarct rats and LV minimum diastolic pressure and LV end-diastolic pressure clearly decreased after infusion of compound [III]. From the result, the compound of the present invention indicates an ability to improve LV diastolic impairment.

As shown above, the results of Practice 3, Practice 4, Experiment 1 and Experiment 2 indicate improvement from the present invention chemical compound [III] for diastolic impairment, cardiac failure due to diastolic dysfunction, and reinforcement of diastolic function.

EXAMPLE 5

Experiment 3

The Effect of Coronary Relaxation from the Formula [III] or [IV] of the Present Invention Porcine heart was purchased without regard of gender. The heart was carried in steep, cool Krebs-Henseleit solution, filled with 95% bubbling oxygen ($O_2$) gas and bicarbonate ($CO_2$) and the left anterior descending coronary artery of 2.5-3 mm diameter was removed. The artery was steeped in the same nutrition solution overnight in a refrigerator and the next day a specimen from a short strip removal in the endothelium (open ring) of width 3 mm was obtained. The specimen was hanged in 10 ml of the organ bath filled with Krebs-Henseleit solution, 95% bubbling oxygen ($O_2$) and bicarbonate ($CO_2$) at 37° C. One side was fixed and the other side was connected to the isometric transducer (T7-8-240, T7-30-240, Olientic) and the change of tension on the amplifier was used for tension recording. After confirming the state for 120 minutes under 1.5 g loading, KCl (40 mM) was added. When the contraction reached a maximum, KCl was washed out. This wash-out was repeated 4 times during the course of 15 minutes. After the stable contraction of KCl was obtained, KCl (30 mM) dissolved in saline was added. The compound [III] or [IV] dissolved in dimethysulfoxide (DMSO) was cumulatively added at 0.01-100 μM after obtaining the continuous contraction. The Krebs-Henseleit solution without the compounds served as the control.

Result: The effect of coronary relaxation was 0% in the control. However, the compound of the present invention [III] or [IV] indicated the effect of coronary relaxation of porcine heart dose-dependently. Data before administration was set at 100% and the data of each after administration was calculated as a percentage change from before administration, with the concentration of chemical compound inducing 50% of relaxation ($EC_{50}\%$) at 42 μM and 100 μM with compound [III] and [IV], respectively.

EXAMPLE 6

Experiment 4

Reducing Effect for the Contractility in the Formula [III] or [IV] of the Present Invention Male guinea pigs, SLC-Hartley strain, weighing 900-1200 g were used in this experiment. After bruising the head, animals were bled to death by performing incisions to the carotid artery. Animal chests were then opened and hearts were removed. Right atriums were removed from the ventricle and a specimen of the right atrium was prepared. The specimen was hanged in 20 ml of the organ bath with full Krebs-Henseleit solution, 95% bubbling oxygen ($O_2$) and bicarbonate ($CO_2$) at 31° C. One side of specimen was fixed and the other side of it was connected to the isometric transducer (TB-651-T: Nihon-Koden Indust.). The beating rate of the spontaneous contraction of the specimen was recorded by the recorder (RECTIGRAPH-8K Nihon Electro Sanei) to evaluate the pharmacological agent. After confirming a stable state for 60-90 minutes under loading of 0.5-1.0 g, the effect of the invention formula [III] or [IV] dissolved by dimethysulfoxide (DMSO) was evaluated to be administered cumulatively at 0.01-100 μM. In the control group, the Krebs-Henseleit solution was used without the test compound. The data before administration was set at 100% and the concentration inhibiting 50% of the maximum contraction ($IC_{50}$ value) was investigated.

Result: In the control group, the inhibition of spontaneous contraction was 9%. The formula [III] or [IV] of the present invention has indicated an effect of inhibition to the right atrium in the guinea pig dose-dependently. The maximum value of contraction width before administration was set at 100% and the concentration of 50% inhibition ($IC_{50}$) of the invention formula [III] or [IV] was 36 μM and 110 μM, respectively.

EXAMPLE 7

Experiment 5

Reducing Effect for the Heart Rate in the Formula [III] or [IV] of the Present Invention Male guinea pigs weighing 900-1200 g were used in this experiment. After bruising the head, animals were bled to death by performing incisions to the carotid artery. Animal chests were then opened and hearts were removed. The right atrium was removed from the ventricle and a specimen of the right atrium was prepared. The specimen was hanged in 20 ml of the organ bath with full Krebs-Henseleit solution 95% bubbling oxygen ($O_2$) and bicarbonate ($CO_2$) at 31° C. One side of the specimen was fixed and the other side of it was connected to the isometric transducer (TB-651-T: Nihon-Kohden Indust.). The beating rate of the spontaneous contraction of the specimen was recorded by the recorder (RECTI-GRAPH-8K Nihon Electro Sanei). The effect of the formula [III] or [IV] of the present invention dissolved in dimethysulfoxide (DMSO) was evaluated for cumulative administration between 0.01-100 μM.

Results: In the control group, the right atrium contraction rate was unable to be reduced. In the formula [III] and [IV] of the present invention, the right atrium contraction rate per minute of the guinea pig was reduced dose-dependently. The 50% inhibition of maximum contraction, set to 100% before administration ($IC_{50}$), was 35 μM and 110 μM with compounds [III] and [IV], respectively.

From the results of 3 experiments, there have been discoveries that the invention formula [III] or [IV] has the effect to dilate the coronary vessels, reduce cardiac contraction and decrease heart rate.

EXAMPLE 8

Experiment 6

Comparison of Heart Rate, LV Pressure and LV Diastolic Function Between the Compound [III] and [II] of the Present Invention (R=H)

Experimental Method

Male Wistar rats weighing 280-300 g were bred. After one week, animals were anesthetized with 3% isoflurane inhalation and respiration was subsequently controlled with an artificial ventilator using 1.7% isoflurane for maintained anesthetization. A micronanometer-tipped pressure catheter (2F, Millar Instruments) was inserted from the right common carotid artery into the left ventricle (LV) and a polyethylene catheter (SP10) for solution injection was inserted from the right femoral vein and the compounds [III] and [II] (R=H) were injected. After confirming stable hemodynamics for 10 minutes, heart rate, LV pressure, and maximal negative first derivative of LV pressure (−dP/dt) were investigated continuously. Each compound [III] or [II] was infused at 0.3 mg/kg/min for 5 minutes. Four rats in each group were evaluated. The solvent used consisted of 0.05% citric acid and 5% sorbitol. Each parameter before and after 5 minutes of administration was determined for 20 heart beats. The results are presented in FIGS. 1, 2 and 3.

Figure 1:
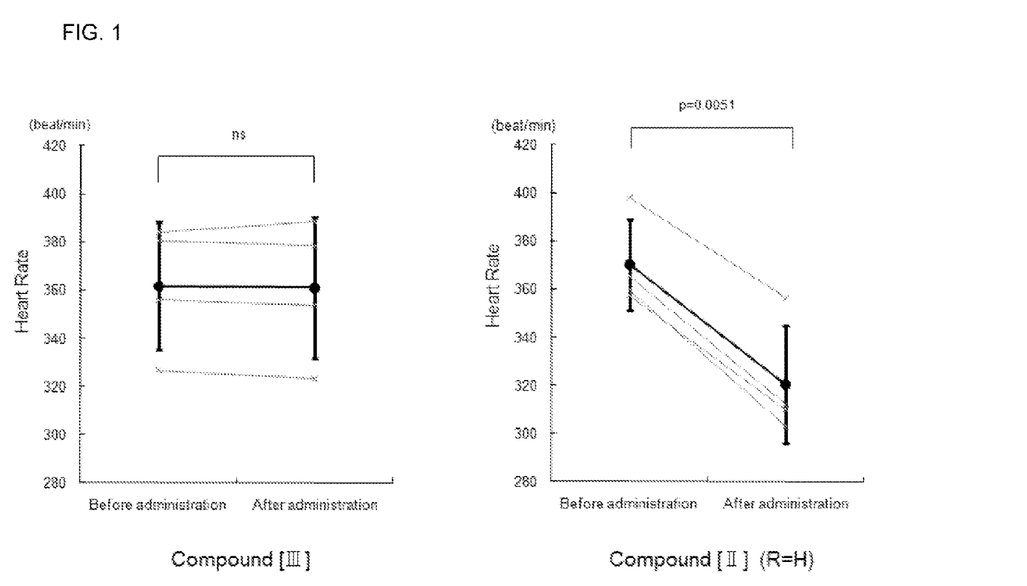
FIG. 1 is a graph showing a comparison of change in heart rate (beats/min) before and after administration of the compounds of the present invention [III], and its basic compound of general formula [II] (R=H).

1) Effect of the Chemical Compounds [III] and [II] of the Present Invention (R=H) for the Heart Beat Heart rate (beat/min) was 361.7±26.5 before administration of the compound [III] of the present invention and 360.9±29.1 after administration, indicating an unrecognizable change. For the other compound, heart rate (beat/min) was 370.1±18.9 before administration of the compound [II] (R=H) and was significantly decreased to 320.2±24.2 after the administration (FIG. 1). There are indications of different pharmacological effects for heart rate between the chemical compounds [III] and [II] of the present invention (R=H).

2) Effect of the Compound [III] and [II] (R=H) for the LV Pressure

Figure 2:
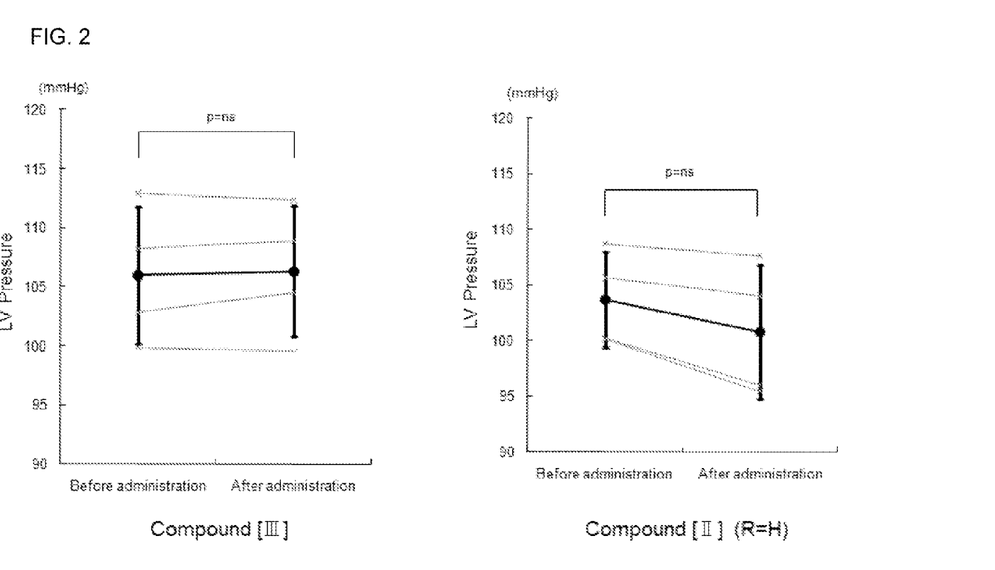
FIG. 2 is a graph showing a comparison of change in left ventricular pressure (mmHg) before and after administration of the compounds of the present invention [III], and its basic compound of general formula [II] (R=H).

LV pressure (mmHg) was 106.0±5.8 before administration of the compound [III] with a slight change to 106.3±5.5 after administration. LV pressure (mmHg) was 103.7±4.2 before administration of the compound [II] (R=H) and was almost the same at 100.8±6.0 after administration (FIG. 2).

3) Comparison of LV Diastolic Function Between the Compound [III] and [II] (R=H)

Figure 3:
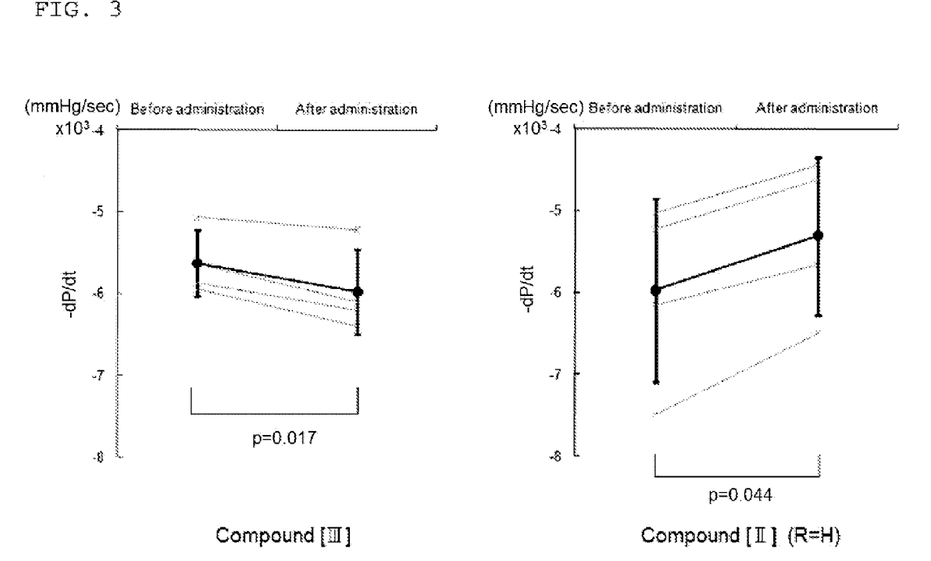
FIG. 3 is a graph showing a comparison of change in cardiac diastolic relaxation function (mmHg/sec) before and after administration of the compounds of the present invention [III], and its basic compound of general formula [II] (R=H).

LV diastolic function (mmHg/sec) was −5631.4±395.9 before administration of the compound [III] and significantly improved to −5982.6±520.1 after administration. For the other, LV diastolic function (mmHg/sec) was −5973.4±1121.3 before administration of the compound [II] (R=H) and significantly decreased to −5311.0±961.4 (FIG. 3).

From the results, the present invention chemical compound is able to improve LV diastolic function compared to the basic compound [II]. However, the basic compound [II] significantly reduced LV diastolic function. There are differences of pharmacological effects for both chemical compounds.

As above, the S-oxide chemical compound indicating the present did not change the heart rate and improved the cardiac diastolic function. In contrast, that basic chemical compound [II] decreased the heart rate and reduced the cardiac function. It is clear that the present invention differs from the basic compound [II] in pharmacological effects, specifically heart rate and cardiac diastolic function.

EXAMPLE 9

Experiment 7

Effect for the Hypertension of the Invent Chemical Compound [III]

Experimental Method

Figure 4:
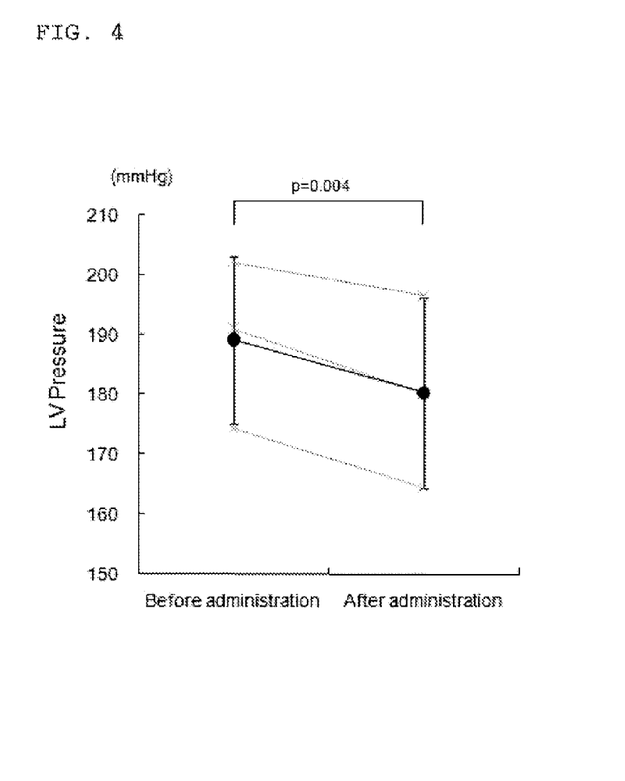
FIG. 4 is a graph showing the comparison of change in left ventricular pressure before and after administration of the present invention [III] on norepinephrine-induced hypertension.

Male Wistar rats weighing 260 g were anesthetized with 3% isoflurane inhalation and respiration was subsequently controlled with an artificial ventilator using 1.7% isoflurane for maintained anesthetization. A micronanometer-tipped pressure catheter (2F, Millar Instruments) was inserted from the right common carotid artery into the left ventricle (LV) and a polyethylene catheter (SP 10) for solution injection was inserted from the right femoral vein and test solutions were injected. After confirming stable hemodynamics for 10 minutes, norepinephrine (20 μg/kg/min) was infused for 10 minutes followed by the infusion of the invention compound [III] (0.1 mg/kg/min) for 10 minutes. This invention compound [III] was infused three times with intervals of 10 minutes each. LV pressure was determined for 20 heart beats before and after administration. The infusion speed of each solution was 16.6 μL/min. The results are shown in FIG. 4. The LV pressure (mmHg) was 189.2±14.0 before this invention compound [III] and significantly decreased to 180.3±14.9 after administration (FIG. 4).

The invention claimed is:
1. A composition, comprising:
   a 1,4-benzothiazepine-1-oxide derivative or a pharmaceutically acceptable salt thereof, the 1,4-benzothiazepine-1-oxide derivative being represented by the following formula [I]:

[I]

wherein R is a hydrogen atom or a hydroxyl group.

2. The composition according to claim 1, wherein the pharmaceutically acceptable salt of 1,4-benzothiazepine-1-oxide derivative is an oxalate.
3. The composition according to claim 1, further comprising a pharmacologically acceptable carrier.
4. A method for treating a cardiac disease and hypertension, comprising:
   administering an effective dose of a composition to patient with the cardiac disease or hypertension,
   wherein the composition comprises a 1,4-benzothiazepine-1-oxide derivative or a pharmaceutically acceptable salt thereof, the 1,4-benzothiazepine-1-oxide derivative being represented by the following formula [I]:

[I]

wherein R is a hydrogen atom or a hydroxyl group, and
wherein the cardiac disease is cardiac failure, angina pectoris, or myocardial infarction.
5. The method according to claim 4,
   wherein the cardiac disease is cardiac failure, and
   wherein the cardiac failure is due to left ventricular diastolic impairment or cardiac relaxation impairment.
6. A method for treating a cardiac failure due to a myocardial relaxation impairment, comprising:
   administering an effective dose of a composition to patient with the cardiac failure due to myocardial relaxation impairment,
   wherein the composition comprises a 1,4-benzothiazepine-1-oxide derivative or a pharmaceutically acceptable salt thereof, the 1,4-benzothiazepine-1-oxide derivative being represented by the following formula [I]:

[I]

wherein R is a hydrogen atom or a hydroxyl group.

* * * * *